US010478521B2

(12) United States Patent
Wolfstaedter et al.

(10) Patent No.: US 10,478,521 B2
(45) **Date of Patent: *Nov. 19, 2019**

(54) ANTIBACTERIAL SHEET MATERIAL THAT CAN BE USED AS A WOUND DRESSING AND METHOD FOR PRODUCING SAME

(71) Applicant: aap Biomaterials GmbH, Dieburg (DE)

(72) Inventors: Marco Wolfstaedter, Woerth am Main (DE); Birgit Schaefer, Babenhausen (DE)

(73) Assignee: aap Implantate AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/383,802

(22) PCT Filed: Feb. 26, 2013

(86) PCT No.: PCT/EP2013/053764

§ 371 (c)(1),
(2) Date: Sep. 8, 2014

(87) PCT Pub. No.: WO2013/135478

PCT Pub. Date: Sep. 19, 2013

(65) Prior Publication Data

US 2015/0125512 A1 May 7, 2015

(30) Foreign Application Priority Data

Mar. 13, 2012 (DE) ........................ 10 2012 004 841

(51) Int. Cl.
*A61L 26/00* (2006.01)
*A61L 31/04* (2006.01)
(Continued)

(52) U.S. Cl.
CPC .......... *A61L 26/0033* (2013.01); *A61K 33/38* (2013.01); *A61L 15/325* (2013.01);
(Continued)

(58) Field of Classification Search
None
See application file for complete search history.

(56) References Cited

U.S. PATENT DOCUMENTS 3,800,792 A * 4/1974 McKnight .............. A61L 15/26 128/DIG. 8
4,294,241 A * 10/1981 Miyata ................. A61L 15/325 128/DIG. 8
(Continued)

FOREIGN PATENT DOCUMENTS

DE 60111240 T2 3/2006
DE 102005044360 A1 3/2007
(Continued)

OTHER PUBLICATIONS

A-B Huang, S-J Xu, G-Y Wei, L Ma, C-Y Gao. "A Trilayer Dermal Equivalent Containing Silver Nanoparticles with Enhanced Antibacterial Property." Chinese Journal of Polymer Science, vol. 27, No. 6, 2009, pp. 865-871.*
(Continued)

*Primary Examiner* — Isaac Shomer
(74) *Attorney, Agent, or Firm* — Kaplan Breyer Schwarz, LLP

(57) ABSTRACT

A sheet material that can be used as a wound dressing and contains elemental metal particles.

5 Claims, 2 Drawing Sheets purifying porcine skin by alkaline and oxidative treatment
↓
acidifying the purified porcine skin
↓
mincing the porcine skin
↓
preparing an aqueous suspension
↓
adjusting the suspension to a pH from 6,5 to 8,5 by adding a phosphate buffer
↓
adding a nano-silver containing aqueous suspension
↓
drying the suspension in trays at T > 20 °C under reduced air pressure
↓
packaging and sterilizing

(51) Int. Cl.

| | |
|---|---|
| ***A61L 15/32*** | (2006.01) |
| ***A61K 33/38*** | (2006.01) |
| ***A61L 31/16*** | (2006.01) |
| ***A61L 15/46*** | (2006.01) |

(52) U.S. Cl.

CPC ............. *A61L 15/46* (2013.01); *A61L 31/044* (2013.01); *A61L 31/16* (2013.01); *A61L 2300/104* (2013.01); *A61L 2300/404* (2013.01); *Y10S 977/773* (2013.01)

(56) References Cited

U.S. PATENT DOCUMENTS

| | | | | |
|---|---|---|---|---|
| 5,110,604 | A * | 5/1992 | Chu et al. | 424/484 |
| 5,331,092 | A | 7/1994 | Huc et al. | |
| 5,785,983 | A * | 7/1998 | Furlan | A61L 15/325 424/423 |
| 7,932,354 | B2 | 4/2011 | Heimann et al. | |
| 8,580,309 | B2 * | 11/2013 | Wilson | A01N 59/16 424/489 |
| 9,849,611 | B2 * | 12/2017 | Wolfstaedter | A61L 31/044 |
| 2003/0035786 | A1 * | 2/2003 | Hendriks et al. | 424/78.17 |
| 2009/0227773 | A1 * | 9/2009 | Heimann | A61L 31/044 530/356 |
| 2012/0225111 | A1 * | 9/2012 | Scholz | 424/444 |
| 2015/0190550 | A1 * | 7/2015 | Nusko | A01N 59/16 424/409 |

FOREIGN PATENT DOCUMENTS

| | | | | |
|---|---|---|---|---|
| DE | 102008062824 | A1 | 7/2010 | |
| DE | 102009059276 | A1 | 6/2011 | |
| DE | 102009053305 | A1 | 8/2011 | |
| EP | 1917982 | A1 | 5/2008 | |
| EP | 1635850 | B1 | 8/2008 | |
| EP | 2098255 | A2 | 9/2009 | |
| WO | 2006000304 | A1 | 1/2006 | |
| WO | WO 2011076203 | A1 * | 6/2011 | A01N 59/16 |
| WO | WO 2012084072 | A1 * | 6/2012 | A61L 24/0015 |

OTHER PUBLICATIONS

K Chaloupka, Y Malam, AM Seifalian. "Nanosilver as a new generation of nanoproduct in biomedical applications." Trends in Biotechnology, vol. 28 No. 11, Nov. 2010, pp. 580-588.*

S Ghosh, R Kaushik, K Nagalakshmi, SL Hoti, GA Menezes, BN Harish, HN Vasan. "Antimicrobial activity of highly stable silver nanoparticles embedded in agar—agar matrix as a thin film." Carbohydrate Research, vol. 345, 2010, pp. 2220-2227.*

R Nusko, G Maier. "Formulation Comprising Metal Nanoparticles." Machine Translation of WO 2011/076203 A1. Original publication in German on Jun. 30, 2011, translation obtained by examiner on Apr. 13, 2016, 29 printed pages.*

CJ Doillon. "Porous Collagen Sponge Wound Dressings: in vivo and in vitro Studies." Journal of Biomaterials Applications, vol. 2, Apr. 1988, pp. 562-578. (Year: 1988).*

H Yang, Z Shu. "The extraction of collagen protein from pigskin." Journal of Chemical and Pharmaceutical Research, vol. 6(2), 2014, pp. 683-687. (Year: 2014).*

"Parent Patent Application in Germany No. DE 10 2012 004 842.4", "Office Action", dated Nov. 6, 2012, Publisher: GPTO, Published in: DE.

"Related International Application No. PCT/EP2013/053763", "International Search Report and Written Opinion", dated May 31, 2013, Publisher: PCT, Published in: EP.

"Related International Application No. PCT/EP2013/053764", "International Search Report and Written Opinion", dated May 31, 2013, Publisher: PCT, Published in: EP.

"Parent Patent Application in Germany: DE 10 2012 004 841.6", "Office Action", dated Nov. 6, 2012, Publisher: GPTO, Published in: DE.

"Office Action" dated Aug. 14, 2015, issued in related U.S. Appl. No. 14/383,811.

"Final Office Action" dated Dec. 24, 2015, issued in related U.S. Appl. No. 14/383,811.

"Office Action" dated Jun. 22, 2016 in related U.S. Appl. No. 14/383,811.

* cited by examiner

ANTIBACTERIAL SHEET MATERIAL THAT CAN BE USED AS A WOUND DRESSING AND METHOD FOR PRODUCING SAME

FIELD OF THE INVENTION

The invention relates to a sheet material with antibacterial properties which is usable as a wound dressing. In particular, the invention relates to a metal-containing collagen material.

BACKGROUND OF THE INVENTION

Sheet materials that can be used as a wound dressing are known. These are in particular collagens which are made of the skin of mammals.

To achieve antibacterial properties, it is known for sheet materials that are usable as a wound dressing to be equipped with antibiotics.

Especially for poorly healing wounds, such as those occurring in particular in case of diabetes and in burn injuries and with multi-resistant germs, antibiotics often fail to achieve sufficient results.

Further, collagen-containing sheet materials are known from practice, which are inoculated with silver in order to provide antibacterial properties.

For this purpose, silver salts are used. A drawback of the silver salts employed is that in many cases nearly all the silver is rapidly released already immediately after application of the sheet material to the wound, so that on the one hand undesirably high toxic levels result in the vicinity of the wound dressing, and on the other the effect does not last long.

Furthermore, the sheet material is often undesirably stained dark by the silver salts used.

OBJECT OF THE INVENTION

The invention is therefore based on the object to produce a sheet material that can be used as a wound dressing and in which the drawbacks of the prior art mentioned above are mitigated.

In particular, the delivery of the metal atoms is to be improved.

SUMMARY OF THE INVENTION

The object of the invention is already achieved by a method for producing a sheet material usable as a wound dressing and by a sheet material in accordance with the illustrative embodiment of the present invention.

The invention relates to a method for producing a sheet material that can be used as a wound dressing. A distinguishing characteristic of such a material is that it is applied on a wound and has a hemostatic effect. For this purpose, films, sponges, or non-woven materials may be used, for example.

The sheet material is produced from a liquid starting material, which means that during manufacturing of the sheet material in at least one manufacturing step the starting material or precursor is a liquid.

This may be either a suspension or a solution.

For example, published patent application EP 2 098 255 A2 (AAP Biomaterials GmbH) discloses a method for producing a porous collagen material. A suspension is prepared from wet-chemically processed and mechanically comminuted mammalian skin. This suspension is the liquid starting material in the sense of the invention.

It is further known from practice to produce collage materials from atelocollagens, which are first dissolved in water. By drying the solution, a collagen-containing sheet material can be produced.

However, the invention additionally relates to alternative materials produced by polymerization.

In particular it is conceivable to produce a sheet material that can be used as a wound dressing from a polysaccharide or from a hyaluronate.

According to the invention, a suspension is added to the liquid starting material, which suspension contains elemental metal particles, i.e. metal particles in non-ionic form. During manufacturing of the sheet material, such as by drying or polymerization, these metal particles are incorporated into the sheet material in elemental form.

In this way, the drawbacks of the use of metal salts as mentioned above are avoided.

At the surface the metals exist in ionic form. By virtue of a small particle size, a large effective surface area can be provided which releases the metal ions to the environment. Due to the use of elemental metals, the ions are continuously released from the surface. Delivery is accomplished evenly distributed over a lengthy period of time.

Metals that are in particular contemplated include silver, gold, zinc, and/or copper. Preferably, silver is used.

In particular a suspension is used which includes metal particles of a mean particle size between 10 nm and 10 μm.

Preferably, nanoparticles with an average particle size of less than 50 nm are used.

The metal particle containing suspension is preferably stabilized with a stabilizing agent such that the metal particles stay suspended over a sufficiently long period of time.

A method for preparing a stable suspension with metal nanoparticles is disclosed, for example, in German patent application DE 10 2009 059 276 A1 (Rent-a-Scientist GmbH). The disclosure of this document is fully incorporated herein by reference with respect to the preparation of the metal particle containing suspension employed.

It will be understood that in the produced sheet material that is usable as a wound dressing these particles may at least in part exist in form of agglomerates.

In a preferred embodiment of the invention, the sheet material is produced by drying the starting material at a temperature above the freezing point of the starting material.

Starting from the teachings of EP 2 098 255 A2 according to which a porous sheet material is produced by lyophilization, drying above the freezing temperature in particular permits to produce a material in which in the present case the collagen settles on the bottom to form a film-like, dense, and ideally at least partially transparent sheet material.

A material with a closed porosity of less than 50%, preferably less than 20%, has the advantage that the metal particles are better retained therein, thereby slowing down the release thereof.

However, it will be understood that a collagen material produced according to the teachings of EP 2 098 255 A2 can likewise be used for the purposes of the invention. This material is highly porous and very flexible and might be preferable over a material of low porosity, depending on the application.

In one embodiment of the invention, the sheet material comprises more than 70%, preferably more than 90% of collagen.

The sheet material may have a thickness from 0.05 to 2.00 mm, preferably from 0.1 to 1.00 mm.

In a preferred embodiment of the invention, the metal particle containing suspension is dosed so that a sheet material is provided with a content of metal particles from 10 to 100,000 ppm, preferably from 100 to 10,000 ppm.

DESCRIPTION OF THE DRAWINGS

The invention will now be explained in more detail with reference to FIG. 1 and FIG. 2.

DETAILED DESCRIPTION

Figure 1:
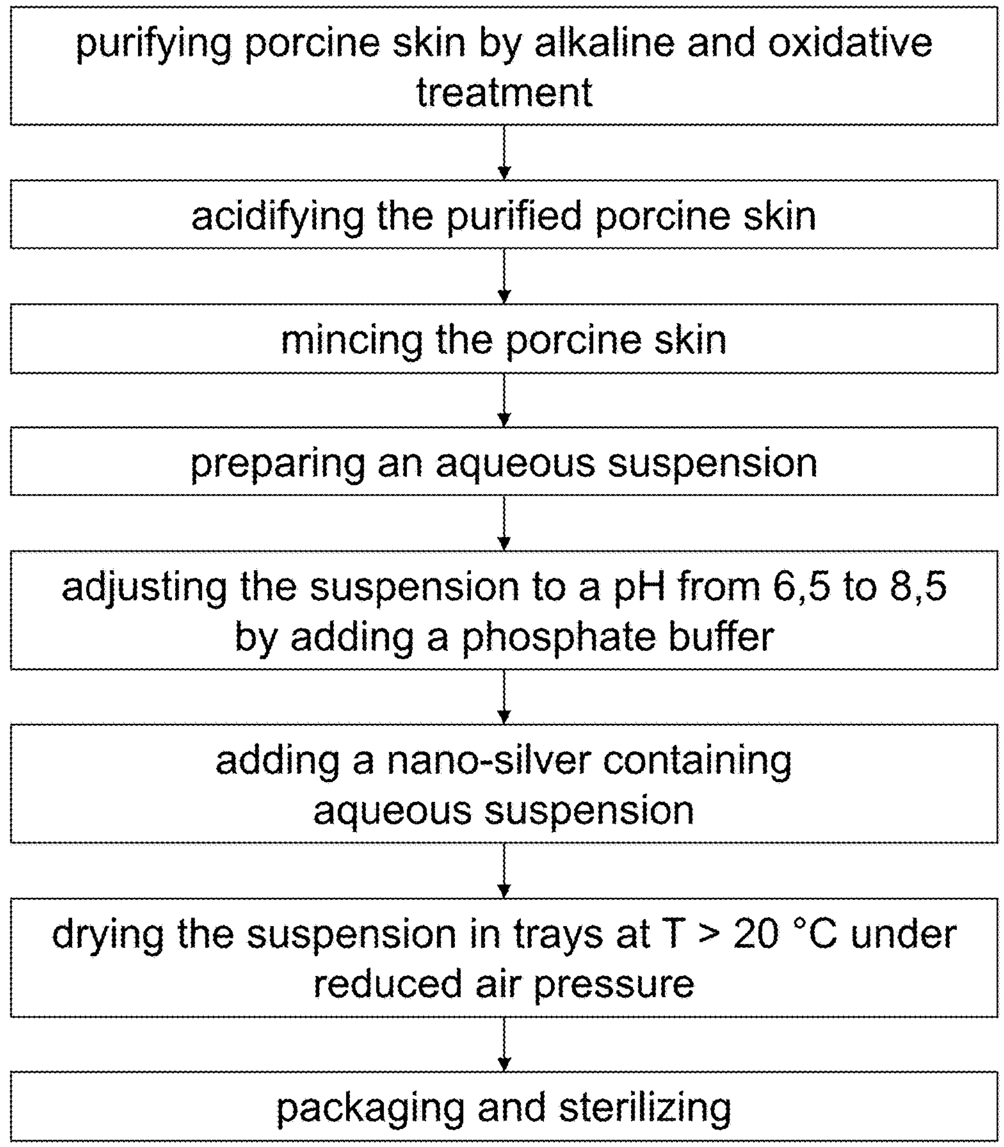
FIG. 1 shows a flowchart of a method for producing a collagen-containing sheet material.

First, porcine skin is prepared by an alkaline and oxidative treatment in FIG. 1.

For this purpose, hydrogen peroxide and sodium hydroxide may be used, for example, in which the starting material is alternately dipped and is then rinsed.

Through this wet chemical preparation, a starting material is provided which comprises more than 70%, preferably more than 80% of collagen.

Then, the wet-chemically purified porcine skin is acidified. Preferably, phosphoric acid is used for this purpose, or another acid such as hydrochloric or acetic acid.

To prepare a suspension, the porcine skin is first comminuted mechanically by mincing, and then an aqueous suspension is produced from the slurry resulting from further comminuting steps. This suspension in particular has a solids content from 0.5 to 5%.

Then, the aqueous suspension is adjusted to a neutral to slightly alkaline pH from 6.5 to 8.5 by adding a phosphate buffer.

Subsequently, a nano-silver containing aqueous suspension is added. For this purpose, a suspension should be used which is stable over a longer period. The metal is not added as a salt, but as elemental silver.

To achieve a good distribution, the addition of the nano-silver containing suspension may be accomplished using suitable dispersion promoting means, for example in an ultrasonic bath, or a rotor-stator type mill.

Subsequently, the suspension is dried in trays at a temperature above 20° C. under vacuum.

The collagen will thereby mostly settle on the bottom of the tray as a film-like structure, with a large part of the silver particles trapped in the material being formed.

Subsequently, the dried sheet material can be packaged and sterilized.

Sterilization may, for example, be accomplished using ethylene oxide, whereby moreover cross-links can be produced in this way which increase the stability of the resulting material.

Also, sterilization of the already packaged material is possible by irradiation. The use of ionizing radiation for sterilization is also possible.

The produced material rehydrates very fast, has a good hemostatic effect, and is foldable, rollable and can be cut easily, even in its dry state.

Additionally, the material is at least translucent to an extent so that the applied material permits to perceive the underlying tissue. Complications such as inflammation arising under the sheet material can be easily identified.

Furthermore, the material is less prone to sticking and can be easily removed.

Figure 2:
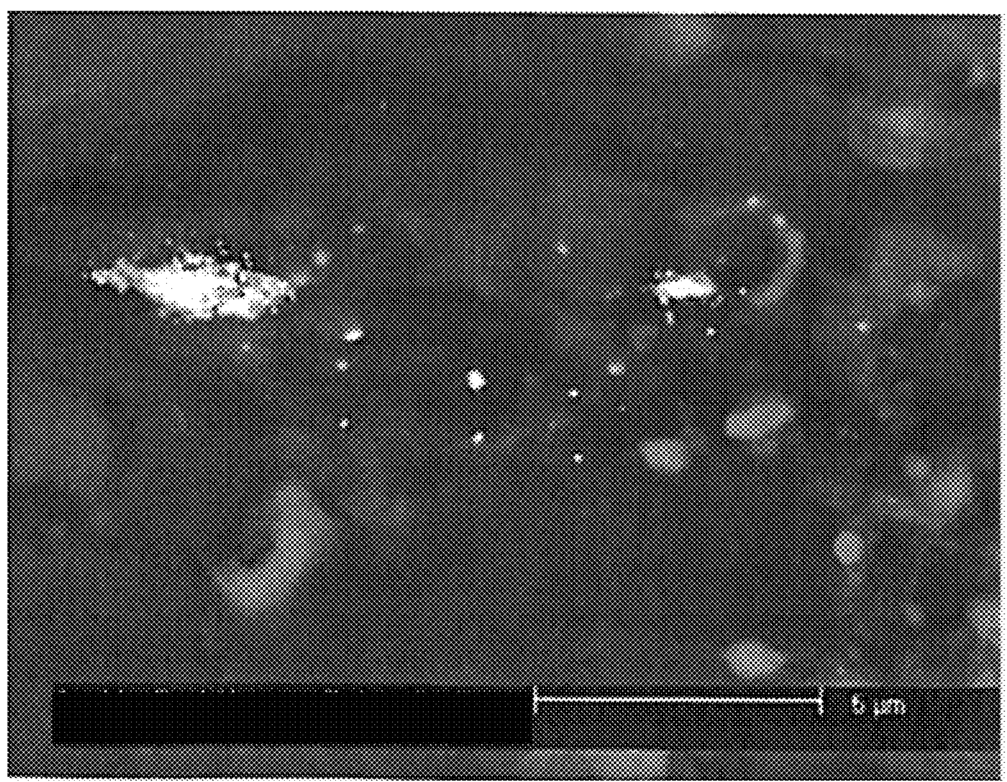
FIG. 2 shows a scanning electron micrograph of a sheet material useable as a wound dressing.

FIG. 2 shows a scanning electron micrograph of a sheet material useable as a wound dressing, which contains about 1000 ppm of nano-silver.

This material was prepared essentially according to the teachings of EP 2 098 255 A2, and after neutralization a silver nanoparticles containing suspension was added to the suspension according to the teachings of DE 10 2009 059 276 A1.

In the scanning electron micrograph, silver particles were found both in surface-near regions and in the middle of the sheet material. This is attributable to the fact that the suspension is stabilized by an emulsifier, so that the silver particles uniformly distribute in the liquid precursor.

Moreover it can be seen that the silver particles are mostly present in form of agglomerates, which does not affect their efficacy.

What is claimed is:

1. A method comprising:

providing porcine skin;

administering an alkaline and oxidative treatment to said porcine skin comprising dipping said porcine skin alternately in hydrogen peroxide and sodium hydroxide;

acidifying the alkaline and oxidatively treated porcine skin with an acid selected from the group consisting of: phosphoric acid, hydrochloric acid, and acetic acid;

mechanically comminuting the acidified porcine skin until a collagen-containing suspension is produced, said suspension having a solids content from 0.5 to 5%;

adjusting said collagen-containing suspension to a neutral to slightly alkaline pH from 6.5 to 8.5 by adding a phosphate buffer;

separately producing an elemental-metal containing suspension that is stabilized with a stabilizing agent, wherein the elemental metal particles include silver particles and have an average particle size between 10 nm and 10 μm;

adding the elemental-metal-containing suspension to the pH-adjusted collagen-containing suspension while promoting dispersion using a dispersion promoting means selected from the group consisting of: an ultrasonic bath, and rotor-stator mill, in order to produce a collagen and elemental metal containing suspension;

drying the collagen-and-elemental-metal-containing suspension until a translucent sheet material is produced, wherein the drying of the liquid collagen-containing starting material is performed at a temperature above 20° C. under vacuum; and sterilizing the dried sheet material using ethylene oxide such that additional cross-links are produced in the sheet material, wherein the elemental metal particles are incorporated into the sheet material both at the near-surface regions and in the middle of the sheet material, wherein the sheet material has a thickness between 0.1 and 1 mm, a closed porosity of less than 50%, an elemental metal particle content from 10 to 100,000 ppm.

2. The method according to claim 1, further comprising applying the sheet material to a wound to dress said wound.

3. The method as claimed in claim 1, wherein the elemental metal particles have an average particle size of less than 50 nm.

4. The method of claim 1, wherein the sheet material has a closed porosity of less than 20%.

5. The method of claim 1, wherein the sheet material comprises more than 90% of collagen.

* * * * *